United States Patent [19]

Johansen

[11] 4,388,406

[45] Jun. 14, 1983

[54] PROCESS FOR ISOLATING CU,ZN-SUPEROXIDE DISMUTASE FROM AQUEOUS SOLUTIONS CONTAINING SAID ENZYME TOGETHER WITH ACCOMPANYING PROTEINS

[75] Inventor: Jack T. Johansen, Rungsted Kyst, Denmark

[73] Assignee: De Forenede Bryggerier A/S, Copenhagen, Denmark

[21] Appl. No.: 315,392

[22] Filed: Oct. 27, 1981

Related U.S. Application Data

[63] Continuation of Ser. No. 149,383, May 13, 1980, abandoned.

[30] Foreign Application Priority Data

May 17, 1979 [DK] Denmark .............................. 2033/79
Apr. 21, 1980 [DK] Denmark .............................. 1687/80

[51] Int. Cl.$^3$ ........................... C12N 9/02; C12N 9/08
[52] U.S. Cl. .................................... 435/189; 435/192; 435/814; 435/815
[58] Field of Search ................ 435/189, 192, 814, 815

[56] References Cited

U.S. PATENT DOCUMENTS 3,758,682 9/1973 Huber et al. ........................ 424/177

OTHER PUBLICATIONS

Goscin et al., Biochim. Biophys. Acta vol. 289, pp. 276-283 (1972).

*Primary Examiner*—Lionel M. Shapiro
*Attorney, Agent, or Firm*—Ladas & Parry

[57] ABSTRACT

Cu,Zn-superoxide dismutase (SOD) is isolated from aqueous solutions containing said enzyme together with accompanying proteins by chromatography of the solution at a pH of 4.7 to 5.5 on a cation exchange resin of the same polarity as SOD in the pH range used. As cation exchange resin may particularly be used carboxymethyl celluloses, cross-liked dextrans substituted with carboxymethyl groups or sulfopropyl groups or cross-linked agaroses substituted with carboxymethyl groups.

The process lends itself to use on an industrial scale and provides a high yield of pure SOD.

2 Claims, No Drawings

PROCESS FOR ISOLATING CU,ZN-SUPEROXIDE DISMUTASE FROM AQUEOUS SOLUTIONS CONTAINING SAID ENZYME TOGETHER WITH ACCOMPANYING PROTEINS

This is a continuation of application Ser. No. 149,383, filed May 13, 1980, now abandoned.

The present invention relates to a process for isolating Cu,Zn-superoxide dismutase (SOD) from aqueous solutions containing said enzyme together with accompanying proteins.

Superoxide dismutases are enzymes catalyzing the dismutation of the superoxide radical, $O_2^-$, to oxygen and hydrogen peroxide:

$$2O_2^- + 2H^+ \rightarrow H_2O_2 + O_2$$

Since 1969 enzymes having this property have been isolated from a large number of different organisms.

Superoxide dismutases containing copper and zinc in their active sites are found in the cytoplasma of eukaryotes. It has been found that these enzymes are dimeric molecules which exhibit a very high degree of homology in their amino acid sequence (C. Petersen et al., Carlsberg Res. Commun. Vol 42, p. 391–395, 1977) and have related physico-chemical properties (A.E.G. Cass et al., Carlsberg Res. Commun. Vol 43, p. 439–449, 1978). Another class of superoxide dismutases containing iron or manganese in their active sites are found in prokaryotes and in eukaryotic mitochondria. In this class there is also a high similarity in amino acid composition and N-terminal amino acid sequence. However, there is no significant homology between the two classes of superoxide dismutases.

The function of the superoxide dismutases is apprarently to protect the cells in aerobic organisms against the toxic effects of the superoxide radical, which is a by-product of the reaction of oxygen in the organism. It is believed that the superoxide radical is involved in various inflammatory processes in the tissues and that it contributes to causing rheumatoid arthritis. It has therefore been proposed to use superoxide dismutase for treating inflammations and perhaps rheumatoid arthritis. The therapeutic effect of Cu,Zn-superoxide dismutase on inflammatory diseases has been confirmed by experiments. It would accordingly be of great importance if it were possible to provide a process for recovering Cu,Zn-superoxide dismutase on an industrial scale in a high yield.

Among the Cu,Zn-superoxide dismutases the bovine enzyme is the most studied. Thus, the complete amino acid sequence and X-ray structure of this enzyme are known. Also, it has been investigated by a variety of spectroscopic methods.

Cu,Zn-superoxide dismutase from beeves and other higher animals has e.g. been recovered from organs and tissues, particularly the liver, by extracting the minced tissue with a cold buffer solution, or from blood by hemolysis of the erythrocytes, in both cases followed by isolation of SOD from the obtained solution of the water soluble proteins. Isolation has e.g. been performed by fractional precipitation with organic solvents or ammonium sulfate, optionally combined with denaturation of heat labile proteins by heating in the presence of divalent metal ions, or by chromatography on diethylamino ethyl cellulose or other ion exchange resins. Generally, low molecular impurities are removed from the purified solution by dialysis and by subjecting it to gel filtration on dextrangel.

From the Danish Pat. No. 131 091 which deals with the recovery of superoxide dismutase from bovine liver it is known to purify the enzyme by passing a solution of the enzyme in a buffer solution of an ionic strength of up to $10^{-2}$ molar concentration and a pH of 5.5 to 8 over a column of an ion exchange resin with either slightly basic or acid groups which attract ions of opposite polarity. One of the general examples of useful resins mentioned is carboxymethyl cellulose, but at pH 5.5 to 8 it has not, as required in the claim, an opposite polarity of SOD, and further the patent provides no examples of the use of carboxymethyl cellulose.

Goscin and Fridovich (Biochim. Biophys. Acta 289, p. 276–283, 1972) recovered Cu,Zn-superoxide dismutase from yeast by the so-called two-phase method, in which after freezing and thawing the yeast cake was stirred in approximately the same volume of a mixture of ethanol and chloroform in the volume ratio of 5:3 for some hours at 25° C., following which the mixture was centrifuged, the clear supernatant was admixed with solid $K_2HPO_4$ and the organic phase salted out was isolated and clarified by centrifugation. Then the proteins were precipitated by adding cold acetone, the precipitate was redissolved in cold phosphate buffer of pH 7,8 and purified of brownish impurities with microgranular diethylamino ethyl cellulose ("DE-32"), and the pale green filtrate was dialyzed against phosphate buffer of pH 7.8 and after clarification by centrifugation chromatographed on a column of "DE-32".

Processing of the aqueous protein solutions in the various processes mentioned above have either failed to provide a sufficiently pure product or have been very complicated and given a too low yield of the pure enzyme.

Accordingly, the object of the invention is to provide a process for isolating SOD from aqueous solutions containing said enzyme together with accompanying proteins which lends itself to use on an industrial scale and gives a very high yield of pure SOD.

This is achieved by the process of the invention which is characterized by subjecting the solution at a pH of 4.7 to 5.5 to chromatography on a cation exchange resin of the same polarity as SOD in the pH range used.

Cation exchange resins of this type known in the art today are mainly various carboxymethyl celluloses, cross-linked dextrans substituted with carboxymethyl groups or sulfopropyl groups, and cross-linked agaroses substituted with carboxymethyl groups.

It has been found that the process of the invention provides a particularly good separation of SOD from other present proteins in aqueous solutions obtained from said various raw materials. This is actually at variance with the theory, according to which ion exchange resins were only to exhibit affinity to substances of opposite polarity. However, the cation exchange resins mentioned and SOD have the same polarity in the pH range used here, and it is therefore surprising that good results are obtained with this process.

As examples of useful cation exchange resins in the process of the invention may be mentioned the carboxymethyl celluloses available under the names "CM-23", and "CM-52" from Whatman Ltd., Great Britain, and under the name "CM-Sephacel" from Pharmacia Fine Chemicals AB, Sweden, the cross-linked dextran substituted with carboxymethyl groups available under the name "CM-Sephadex" from Pharmacia Fine Chemicals AB, the cross-linked dextran substituted with sulfopropyl groups available under the name "SP-Sephadex" from Pharmacia Fine Chemicals AB, and the cross-linked agarose substituted with carboxymethyl groups available under the name "CM-Sepharose CL 6B" from Pharmacia Fine Chemicals AB.

Chromatography of the solution on a cation ion exchange resin may optionally be effected batch-wise by stirring the ion exchange granulate into the solution, but it is carried out most advantageously as a column procedure which is easier to work with on a larger scale and ensures that all the enzyme is adsorbed on the ion exchanger.

After purification of the solution by ion exchange chromatography in accordance with the invention the active fractions of the eluate may be further purified in a known manner by gel filtration or fractional alcohol precipitation and be subjected to one or more additional chromatographies in a known manner, or, preferably, by the process of the invention following which the active fractions are dialyzed against distilled water and concentrated to dryness, preferably by freeze drying.

The process of the invention will be illustrated more fully in the following examples.

EXAMPLE 1

2.5 l of diethyl ether were added to 20 kg of bakers' yeast (Saccharomyces cerevisiae) and the mixture was left for 30 minutes to make stirring possible. After stirring for about 2 hours at 25° C. 20 l of hot water were added, pH was adjusted to 7.5 and stirring was continued for 4 hours at 45° C. After stirring for another 16 hours with a drop in temperature to 25° C. pH was adjusted to 4.8 and the suspension was clarified by centrifugation at 2000 G for 30 minutes.

To remove low molecular weight compounds the supernatant was diluted 5-fold with 0.01 M sodium acetate buffer at pH 4.8 and concentrated to 10 l by ultrafiltration. The latter procedure was performed twice.

1 l of microgranular carboxymethyl cellulose (available under the name "CM-52" from Whatman Ltd.) which had been equilibrated with 0.025 M sodium acetate buffer at pH 4.8 was added to the concentrated solution, and the mixture was stirred for 1 hour. The carboxymethyl cellulose was collected on a column of 30 cm diameter, washed with 10 l of 0.025 M sodium acetate buffer at pH 4.8, and transferred to a column of 10 cm diameter. The column was eluted with a linear gradient of sodium acetate (0.025→0.200 M) at pH 4.8 in a total volume of 6 l. The flow rate was 400 ml/h and fractions of 30 ml were collected. The active fractions which were intensively red were collected and the pool was concentrated by ultrafiltration before freeze drying.

The freeze-dried sample was redissolved in 50 ml of 0.025 M sodium acetate buffer at pH 4.8 and applied to a 5×40 cm column of dextrangel (available under the name "Sephadex G-50 superfine" from Pharmacia Fine Chemicals AB) equilibrated against the acetate buffer. The column was eluted with 1 l of 0.025 M sodium acetate solution at pH 4.8 and fractions of 5 ml were collected. The flow rate was 110 ml/h. A visible result of the gel chromatography was that the green Cu,Zn-superoxide dismutase separated from the red heme protein, although the two bands were lying very close.

The active fractions were pooled and applied to a 5×10 cm column of "CM-52" equilibrated with 0.025 M sodium acetate solution pH 4.8. The column was eluted with a linear gradient of sodium acetate (0.025→0.200 M) at pH 4.8. A total volume of 1200 ml was applied with a flow rate of 200 ml/h, and fractions of 6 ml were collected. The active fractions were pooled, dialyzed against distilled water, and freeze dried.

The gel filtration step can be replaced by an alcohol precipitation step. The freeze dried sample from the "CM-52" batch step is dissolved in 100 ml of 0.005 M potassium phosphate buffer at pH 7.0 and 67 ml of ethanol are slowly added. After 10 minutes centrifugation at 13000 r.p.m. another 166 ml of ethanol are added to the supernatant. The precipitate is collected by centrifugation for 15 minutes at 13000 r.p.m. and redissolved in 50 ml of 0.025 M sodium acetate buffer at pH 4.8. The sample is then applied to a "CM-52" column as described above, and the active fractions are dialyzed against distilled water and freeze-dried. The results of the purification procedure and summarized in the following table I.

TABLE I

| | Purification of Cu,Zn—superoxide dismutase from 20 kg of yeast | | | | | | | |
|---|---|---|---|---|---|---|---|---|
| Fraction | Protein conc. (mg/ml) | Total volume (ml) | Total protein (mg) | Activity (units/ml) | Total units | Yield (%) | Specific activity (units/mg) | Fold purication |
| Lysate, pH 4.8 | 20 | 28 000 | 560 000 | 1090 | $3,05 \times 10^7$ | 100 | 55 | 1 |
| Concentrate from ultrafiltration | 18,1 | 17 000 | 308 000 | 962 | $1,64 \times 10^7$ | 54 | 53 | 1 |
| Comb. fractions from "CM-52" batch | 2,0 | 985 | 1 970 | 12600 | $1,24 \times 10^7$ | 41 | 6300 | 115 |
| Comb. fractions from "G=superfine" | 15,0 | 95 | 1 420 | $1,29 \times 10^5$ | $1,22 \times 10^7$ | 40 | 8600 | 156 |
| Comb. fractions from "CM-52" column | 5,48 | 208 | 1 140 | $5,06 \times 10^4$ | $1,05 \times 10^7$ | 34 | 9230 | 168 |
| Alternative procedure: | | | | | | | | |
| Redissolved alcohol precipitate | 27,3 | 50 | 1 360 | $2,20 \times 10^5$ | $1,10 \times 10^7$ | 36 | 8090 | 147 |
| Comb. fractions from "CM-52" column | 8,07 | 132 | 1 070 | $7,51 \times 10^4$ | $9,91 \times 10^6$ | 32 | 9300 | 169 |

It appears that the yield of the "CM-52" fractionation, providing a purification of 115 times in relation to the concentrate from the ultrafiltration, was 75% of the total number of units in the concentrate. When the cation exchange chromatography was carried out in the same manner using a plurality of other cation exchange resins of the desired properties, the yields listed in table II were obtained.

TABLE II

| Cation exchange resin | Yield of SOD |
|---|---|
| "CM-52" | 75% |
| "CM-23" | 61% |
| "CM-Sephadex-C50" | 75% |
| "CM-Sephadex-CL-6B" | 85% |
| "SP-Sephadex" | 64% |

EXAMPLE 2

Hemolysis and precipitation of hemoglobin 7 liters of decanted blood that still contained about 2 l of plasma and thus corresponded to about 5 l of packed blood cells, were admixed with 7 l of 96% ethanol under vigorous stirring. After 1 hour 15 l of deionized water were added, and stirring was continued for 30 minutes.

The suspension was centrifuged in a MSE basket centrifuge at approx. 2000 rpm. and the cake of hemoglobin was washed with 2 l of water before the centrifuge was emptied. 29.5 l of supernatant was obtained.

Isolation of carbonic acid anhydrase

The supernatant was applied to a 10×12 cm column of the affinity matrix "Sepharose"-glycyl-tyrosine-azobenzenesulfonamide that specifically adsorbs carbonic acid anhydrase, but does not adsorb SOD and catalase. After washing of the affinity matrix the carbonic acid anhydrase was eluted with an aqueous 0.2 M potassium thiocyanate solution containing 0.05 M "Tris" sulfate and having a pH of 6.5.

Isolation of SOD and catalase

The solution that contained SOD and catalase was adjusted to pH 4.75 with 1 M acetic acid, and passed through a 20 cm diameter column, packed with 2 l of "CM-23" equilibrated in 20 mM Na-acetate buffer, pH 4.8. The flow rate was approx. 15 l per hour. The ion exchanger was then washed with 15 l of 20 mM Na-acetate buffer, pH 4.8.

The column was eluted with a linear gradient of 3 l of 100 mM and 3 l of 200 mM Na-acetate, pH 4.8, at a flow rate of 1.5 l per hour. SOD was eluted at about 150 mM Na-acetate.

Catalase was eluted with 0.1 M Na-phosphate buffer, pH 7.0.

The SOD and catalase containing fractions were separately pooled and ultrafiltrated on a "DDS 600" membrane in a "DDS MF cell", both available from De danske Sukkerfabriker A/S.

SOD purification

The SOD solution was diafiltrated using a 10 mM Na-phosphate buffer, pH 7.5, and further purified by chromatography on a "DE-52" column (5×8 cm), equilibrated in a 10 mM Na-phosphate buffer, pH 7.5. The column was developed with a linear gradient of 2×600 ml of 10 mM Na-phosphate buffer, pH 7.5, containing 0→0.125 M NaCl. The flow rate was 110 ml per hour, and fractions of 10 ml were collected.

The SOD containing fractions were pooled. Specific activity and absorption spectrum showed that the enzyme was pure.

Catalase purification

The catalase solution from the ultrafiltration was purified by $(NH_4)_2SO_4$ fractionation.

Regeneration of the "CM-23" column

After elution of the catalase 3 l of 0.5 M NaOH solution were passed through the column followed by 3 l of water. Then 3 l of 0.5 M hydrochloric acid were passed through the column followed by 3 l of water and 3 l of 0.2 M Na-acetate buffer, pH 4.8.

The column was then treated with 20 mM Na-acetate buffer, pH 4.8, until the conductivity and pH of the eluate were the same as those of the buffer. The column was then ready for use again.

Results

A survey of the purification steps carried out and the yields of SOD, catalase and carbonic acid anhydrase is given in table III below.

TABLE III

Isolation and purification of SOD, catalase and carbonic acid anhydrase from 5 liters of red blood cells

| | Volume (liter) | SOD (mg) | Yield (%) | Catalase (mg) | Yield (%) | Carbonic acid anhydrase (mg) | Yield (%) |
|---|---|---|---|---|---|---|---|
| 1. 7 liters of decanted blood + 7 liters of ethanol | 14 | | | | | | |
| 2. Addition of 15 liters of water | 29 | | | | | | |
| 3. Centrifugation and washing | 29.5 | 365 | 100 | 1600 | 100 | 11 000 | 100 |
| 4. Affinity chromatography and elution of carbonic acid anhydrase | 2 | | | | | 10 000 | 90 |
| 5. Column "CM-23" and elution of SOD | 1.3 | 300 | 82 | | | | |
| 6. Elution of catalase | 2 | | | 1400 | 87 | | |
| 7. Ultrafiltration of SOD solution | 0.25 | 290 | 79 | | | | |
| 8. Column "DE-52" and elution | 0.30 | 290 | 79 | | | | |

I claim:

1. A process for isolating Cu,Zn-superoxide dismutase (SOD) from aqueous solutions containing said enzyme together with accompanying proteins, characterized by subjecting the solution at a pH of 4.7 to 5.5 to chromatography on a cation exchange resin of the same polarity as SOD in the pH range used.

2. A process according to claim 1, characterized by using as cation exchange resin carboxymethyl celluloses or cross-linked dextrans substituted with carboxymethyl groups or sulfopropyl groups or cross-linked agaroses substituted with carboxymethyl groups.

* * * * *